(12) United States Patent
Fressinet et al.

(10) Patent No.: US 7,875,168 B2
(45) Date of Patent: Jan. 25, 2011

(54) DEVICE FOR CALCULATING BLOOD FLOW IN AN EXTRACORPOREAL BLOOD CIRCUIT, AND AN APPARATUS FOR TREATMENT OF BLOOD USING THE DEVICE

(75) Inventors: Jean Louis Fressinet, Saint Jean de Touslas (FR); Massimo Zaccarelli, San Felice sul Panaro (IT); Gianluca Artioli, Mirandola (IT); Jeffrey J. Letteri, Punta Gorda, FL (US)

(73) Assignee: Gambro Lundia AB (SE)

( * ) Notice: Subject to any disclaimer, the term of this patent is extended or adjusted under 35 U.S.C. 154(b) by 900 days.

(21) Appl. No.: 10/975,082

(22) Filed: Oct. 28, 2004

(65) Prior Publication Data
US 2005/0095171 A1 May 5, 2005

Related U.S. Application Data

(60) Provisional application No. 60/568,068, filed on May 3, 2004.

(30) Foreign Application Priority Data
Oct. 29, 2003 (IT) .......................... MO2003A0293

(51) Int. Cl.
*B01D 65/00* (2006.01)
(52) U.S. Cl. .................... 210/87; 210/103; 210/134; 210/321.65; 210/645; 417/5; 417/44.1; 604/5.01; 604/6.09; 604/65; 604/67
(58) Field of Classification Search ............ 210/86, 210/87, 97, 101, 103, 134, 646, 198.1, 321.6, 210/321.65, 645; 604/5.01, 6.09, 30, 65, 604/67, 131, 246, 6.01, 19, 27, 28, 31; 417/2–6, 417/18–22, 42, 43, 44.1
See application file for complete search history.

(56) References Cited

U.S. PATENT DOCUMENTS 4,370,983 A * 2/1983 Lichtenstein ................ 600/301

(Continued)

FOREIGN PATENT DOCUMENTS

EP 0 317 766 12/1992

(Continued)

OTHER PUBLICATIONS

International Search Report for International Patent Application No. PCT/IB2004/003307.

*Primary Examiner*—Joseph W Drodge
(74) *Attorney, Agent, or Firm*—Finnegan, Henderson, Farabow, Garrett & Dunner, LLP

(57) ABSTRACT

The invention relates to a device for calculating blood flow and to an apparatus for extracorporeal blood treatment provided with the device. The device includes a memory for receiving and storing either a first datum relating to a blood flow removed from the patient $Q_b$, or a second datum relating to a flow of liquid Qt crossing a tract of the extracorporeal circuit, and a third datum relating to a flow of infusion liquid $Q_{inf}$ flowing through the infusion line. The device also comprises a control unit able to calculate the first datum or the second datum as a function of the third datum relating to the flow of infusion liquid $Q_{inf}$.

23 Claims, 4 Drawing Sheets

U.S. PATENT DOCUMENTS

| | | | |
|---|---|---|---|
| 4,490,135 A | 12/1984 | Troutner | |
| 4,500,309 A | 2/1985 | Diederich et al. | |
| 4,923,598 A | 5/1990 | Schäl | |
| 5,200,090 A * | 4/1993 | Ford et al. | 210/739 |
| 5,330,425 A | 7/1994 | Utterberg | |
| 5,344,568 A | 9/1994 | Kitaevich et al. | |
| 5,366,630 A * | 11/1994 | Chevallet | 210/645 |
| 5,421,812 A | 6/1995 | Langley et al. | |
| 5,573,505 A | 11/1996 | Johnson et al. | |
| 5,665,061 A | 9/1997 | Antwiler | |
| 5,676,841 A | 10/1997 | Brown | |
| 5,910,252 A * | 6/1999 | Truitt et al. | 210/645 |
| 6,471,872 B2 * | 10/2002 | Kitaevich et al. | 210/739 |
| 6,743,191 B1 | 6/2004 | Chang | |
| 6,780,322 B1 * | 8/2004 | Bissler et al. | 210/637 |
| 6,793,643 B1 * | 9/2004 | Briggs | 604/6.08 |
| 6,814,864 B1 * | 11/2004 | Favre et al. | 210/321.65 |
| 7,112,273 B2 * | 9/2006 | Weigel et al. | 210/143 |
| 2004/0129638 A1 | 7/2004 | Chang et al. | |

FOREIGN PATENT DOCUMENTS

| | | |
|---|---|---|
| EP | 0 611 228 | 8/1994 |
| EP | 0 578 175 | 10/1998 |
| EP | 0 829 265 | 9/2001 |
| WO | WO 00/64456 | 11/2000 |

* cited by examiner

DEVICE FOR CALCULATING BLOOD FLOW IN AN EXTRACORPOREAL BLOOD CIRCUIT, AND AN APPARATUS FOR TREATMENT OF BLOOD USING THE DEVICE

CROSS REFERENCE TO RELATED APPLICATIONS

This application claims the priority of Italian Patent Application No. MO2003A000293, filed Oct. 29, 2003, and the benefit of U.S. Provisional Application No. 60/568,068, filed on May 3, 2004, the contents of both of which are incorporated herein by reference.

FIELD OF THE INVENTION

The invention relates to a device for determining the blood flow in an extracorporeal circuit, and to an apparatus for blood treatment using the device. In particular, the device of the invention is usefully applied in apparatus for extracorporeal treatment of blood such as for example apparatus for hemodialysis, hemofiltration, hemodiafiltration, plasmapheresis, separation of undesired agents, etc.

BACKGROUND OF THE INVENTION

As is known, apparatus for extracorporeal treatment of blood comprise, in use configuration, an extracorporeal circuit through which blood taken from a patient is sent towards a treatment unit before being returned to the patient.

A typical extracorporeal circuit comprises a blood removal branch (taking blood from the patient) which is connected to a first chamber of a treatment unit, and a second branch, a return branch, which is connected to an outlet of the first chamber and returns the blood to the patient. A pump operates at the first and/or the second branches, which pump is predisposed to move the blood through the circuit.

In a most typical configuration, the pump, for example a peristaltic pump, acts on a tract of the removal branch line upstream of the treatment unit. The treatment unit also comprises a second chamber, separated from the first chamber by a semi-permeable membrane, towards which the solid particles and the excess liquid to be removed from the patient's blood are drawn.

Also known are some therapies or treatments which can be carried out with the apparatus of the above-described type which require use of one or more infusion lines of liquids of various natures, according to the type of treatment being carried out. An infusion line typically comprises a source of liquid to be infused (for example a bag or preparation circuit in the liquid line), an infusion tube which can be associated to a pump or another flow-regulating organ, and an infusion point which can be directly connected to the cardiovascular system of the patient or to a predetermined point in the extracorporeal circuit.

Reference is made in particular to pre-dilution infusion, when the infusion line is connected to the blood removal branch upstream of the treatment unit, and to post-dilution infusion, when the line is connected to the blood return branch to the patient.

Independently of the type of treatment carried out and of the presence and configuration of the infusion lines, a value which it is important to know is the effective flow rate of the blood removed from the patient and treated by the machine. Normally the operator sets the flow rate and the machine displays the set flow-rate, checking that the actual flow rate follows, with a certain degree of approximation, the set rate.

Normally the blood circuit is provided with a flow sensor which acts on the extracorporeal circuit and is able to provide a signal to send to a control unit which regulates the blood pump. For example, the blood pump can be associated to a revolution counter, or angular velocity sensor, able to generate a signal which is then processed by the control unit to provide an indication of the blood flow and thus the pump speed can be corrected, if necessary.

The applicant has found that there are certain configurations in which the total flow rate when calculated as described above does not provide a datum relating to the flow rate actually as removed from the patient; for example, a particular configuration is achieved when the blood pump operates in a tract of the blood removal branch while a pre-dilution infusion line is connected to a portion of the blood removal branch upstream of the tract of tubing in which the pump operates.

In this configuration a reading of the blood flow rate effectively taken from the patient based on the angular velocity of the pump leads to a wrong calculation: it is indeed true that the liquid crossing the tract of tubing in which the pump operates comprises blood coming from the patient plus liquid coming from the infusion line or lines which are connected to the tract of tubing upstream of the blood pump.

More generally, when the calculation of the blood flow rate taken from the patient and treated in the extracorporeal blood circuit is derived from a sensor and/or control unit acting in a tract of tubing in the extracorporeal circuit which is located downstream of a point where a liquid line enters the circuit, the flow rate of the liquid line causes an error in the calculation of the blood flow rate.

A main aim set by the applicant is thus to calculate by a simple method a blood flow rate which is effectively that which is removed from the patient, in cases where there is an infusion line placed as described above.

A further aim is to provide a technical solution which is able automatically to guarantee a desired flow rate in a blood removal operation on a patient, independently of the presence of any liquid infusion upstream of the means destined to cause the liquid to circulate in the extracorporeal circuit.

A further aim of the invention is to provide a device which informs about and controls the ratio between the true blood flow rate extracted from a patient and the flow rate of any line destined to flow into the extracorporeal circuit upstream of the blood pump.

A further aim is to provide a simple device which operates with traditional sensor means, present in apparatus for blood treatment.

In addition to the foregoing, a further aim of the invention is to provide a device which operates both in the case where the flow rates of the blood pump and the pre-infusion lines are predetermined by the user, and in the case where one or more of the flow rates are not predetermined.

One or more of the above-mentioned technical aims are attained by a device for determining a blood flow rate in an extracorporeal blood circuit and by an apparatus for extracorporeal blood treatment comprising the infusion device, according to what is described in one or more of the appended claims.

BRIEF DESCRIPTION OF THE DRAWINGS

Further characteristics and advantages will better emerge from the detailed description that follows of a preferred but not exclusive embodiment of the device for determining a blood flow in an extracorporeal circuit and of an apparatus for extracorporeal blood treatment comprising the device, in accordance with the present invention.

The description will be made herein below with reference to the appended figures of the drawings, provided by way of a non-limiting example, in which.

DETAILED DESCRIPTION OF THE INVENTION

Figure 1:
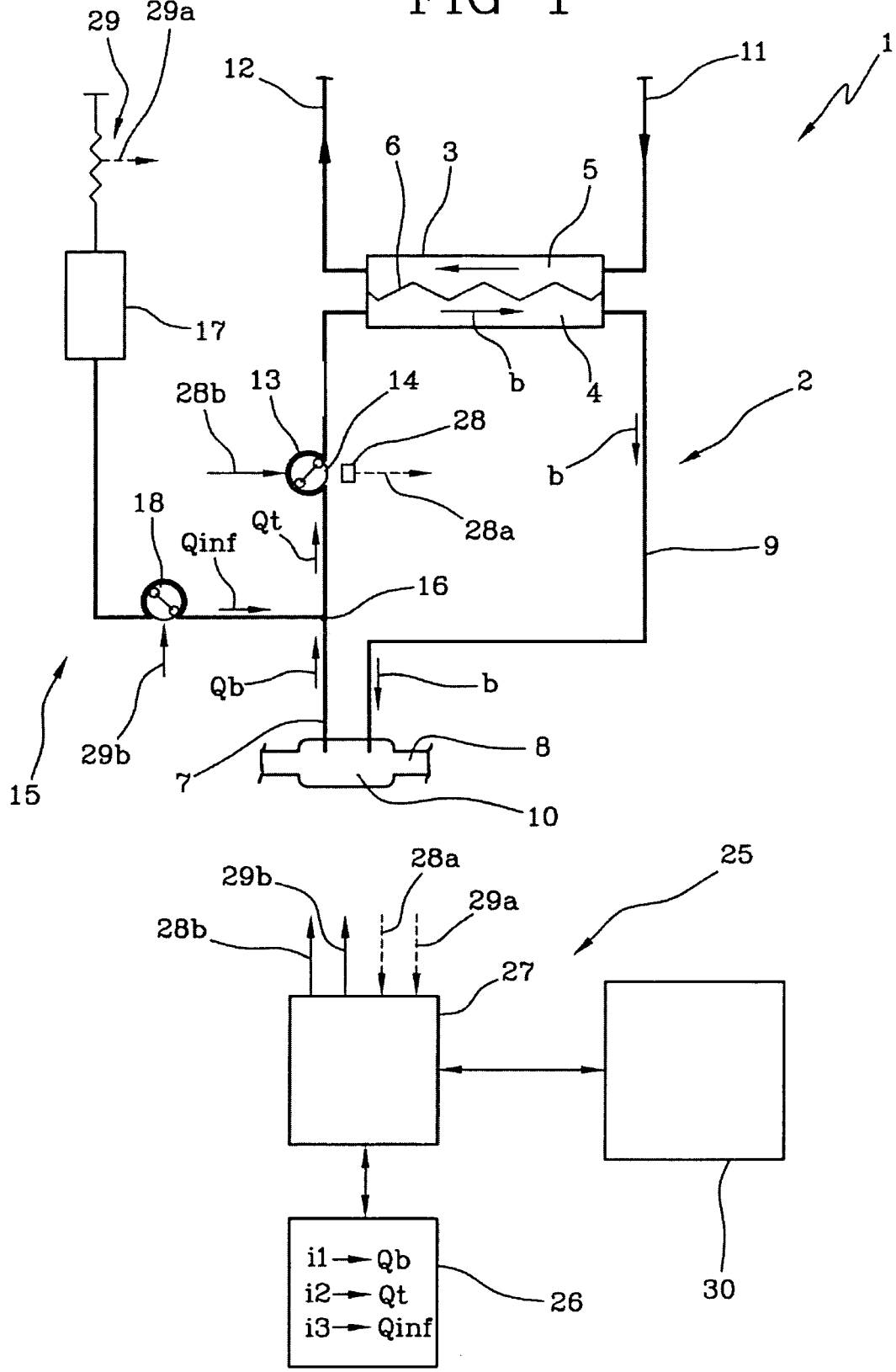
FIG. 1 is a schematic view of a first apparatus for extracorporeal blood treatment comprising the device for calculating the blood flow rate of the present invention.
Figure 2:
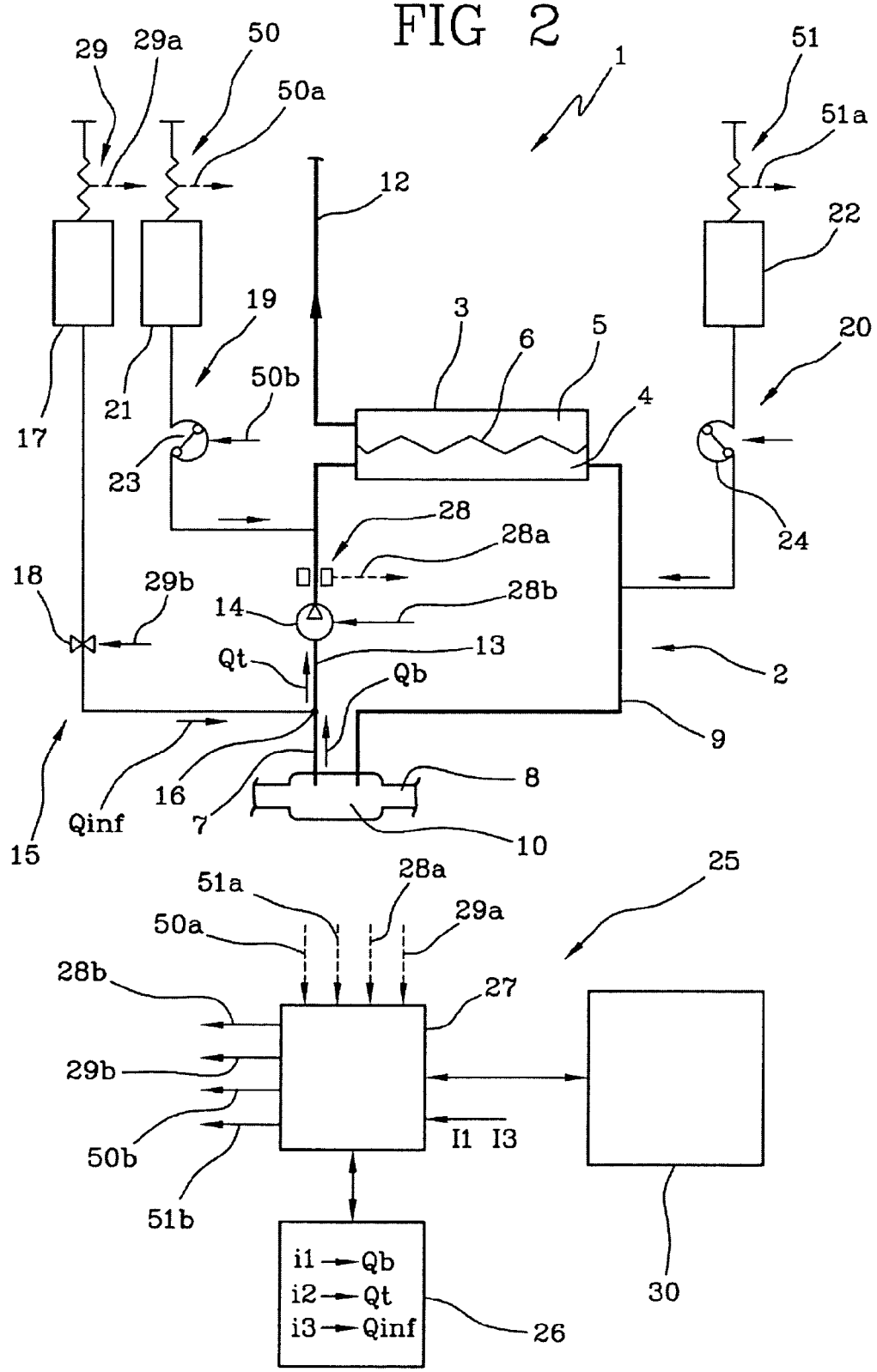
FIG. 2 is a schematic view of a second apparatus for extracorporeal blood treatment comprising the device for calculating the blood flow rate of the present invention.

With reference to the figures of the drawings, 1 denotes in its entirety an apparatus for extracorporeal blood treatment according to the present invention. The apparatus 1 comprises an extracorporeal circuit 2 for circulation of blood provided with at least one blood treatment unit 3 having a first and a second chamber 4, 5 separated by a semi-permeable membrane 6; the circuit 2 exhibits a blood removal branch 7 having an end destined to be connected with a cardiovascular system 8 of a patient and a further end in communication with an inlet of the first chamber 4, and at least one blood return branch 9, having an end destined to be connected with the cardiovascular system and a further end in communication with an outlet of the first chamber 4. In the accompanying figures of the drawings the ends of the blood removal branches connected to the patient are connected up to a fistula 10. Other vascular accesses, however, could be used. The blood treatment unit can be a filter for hemodialysis, or a filter for hemofiltration, or a filter for hemodiafiltration, or a filter for plasmapheresis, or a filter for ultrafiltration, or a unit for subjecting the blood to any physical or chemical treatment which requires a practically constant blood removal to be made from a patient or a donor. In addition to this, the circuit can comprise one or more of the above-mentioned treatment units according to the type of treatment the blood is to undergo. FIG. 1 schematically represents a filter 3 for hemodiafiltration, comprising a second chamber to which is connected, in inlet, a fresh dialysis liquid, and in outlet a discharge line. FIG. 2 illustrates an apparatus 1 with a filter 3 for hemofiltration. In this case no fresh dialysis liquid in inlet to the second chamber is included.

First movement means 14 is associated to a predetermined tract 13 of the extracorporeal circuit 2 for causing a flow of liquid through the predetermined tract 13. The first movement means 14 can comprise at least one pump, for example a rotary pump of the peristaltic type, as shown in FIG. 1, or other means able to cause a flow of liquid in the extracorporeal circuit. By way of non-limiting illustration, the means could be pumps or organs comprising active elements which constrict the tract of tubing associated to the pump to advance the fluid, or the means could also be pumps crossed by the fluid as schematically illustrated in FIG. 2. In the examples shown in FIGS. 1 and 2 the movement means operate on the blood removal branch; however they can also operate exclusively on the return branch, or means can be disposed on both branches. The apparatus 1 exhibits an infusion line 15 connected to the extracorporeal blood circuit at an infusion section 16 located upstream of the predetermined tract 13 on which the blood pump 14 operates, with reference to the direction of circulation of the blood in the extracorporeal circuit indicated by arrows "b". The infusion line illustrated in the accompanying figures of the drawings comprises at least one container 17 of a liquid to be infused; note that similarly a liquid in-line preparation system can be used, which does not require pre-prepared bags or containers.

Second movement means 18 operates in correspondence of the infusion line 15, causing an infusion liquid flow through the infusion line. The second means 18 can comprise a peristaltic pump, as in the example of FIG. 1, or other organs able to determine a flow of liquid. For example, in FIG. 2 the container of infusion liquid is installed at a upstream of the section where the infusion line meets the blood removal branch: in this case the second movement means comprise a support (not illustrated and for example comprising a support rod, a part of the machine frame or the like) for correctly positioning the bag at the desired height so as to use gravitation to cause the liquid to fall and a regulation organ, for example a manually- or automatically-activated valve, on the infusion line. In accordance with other embodiments, not illustrated, the infusion pump can comprise one or more syringes or a normal positive-displacement pump crossed by the flow of liquid to be pumped.

The apparatus 1 can comprise other infusion lines apart from the one described. The example of FIG. 2 illustrates an embodiment having two further infusion lines 19, 20, one connected to the removal line and the other to the return line. Each of the further infusion lines 19, 20 comprises a respective container for a liquid to be infused 21, 22, and a respective infusion pump 23, 24. Obviously, also in this case an in-line infusion liquid production can be provided, using movement means of the fluid which are different from those illustrated by way of example here.

Still with reference to the figures of the drawings, $Q_b$ denotes the blood flow removed from the patient, $Q_t$ the overall flow of liquid across the tract 13 downstream of the infusion section 16 and $Q_{inf}$ the infusion liquid flow crossing the infusion line 15 coming from the infusion section 16.

In the following description "s" will denote nominal values set by the user for flows $Q_b$, $Q_{inf}$, $Q_t$, "r" will denote the actual values measured by sensors for the same flows, and "c" will indicate values of those flows calculated on the basis of the settings and/or the measurements of the actual values of the flows, as will be better described herein below.

As the figures of the drawings schematically illustrate, the apparatus 1 is provided with a blood flow calculation device 25 comprising at least one memory 26 and at least one control unit 27, for example a microprocessor, connected to and cooperating with the memory 27. Alternatively the control unit 27 can be of an analog type.

The memory is configured to receive and store one or more of the following data: a first datum (i1), relating to the blood flow removed from the patient $Q_b$, a second datum (i2), relating to the flow of liquid $Q_t$ across the tract 13 and a third datum (i3), relating to an infusion liquid flow $Q_{inf}$ crossing the infusion line 15. According to the embodiment of the invention, each datum i1, i2, i3 can comprise one or more values relating respective to the blood flow removed from the patient $Q_b$, the liquid flow $Q_t$ across the tract 13 and the infusion liquid flow $Q_{inf}$ crossing the infustion line 15, for example actual values of each flow measured with appropriate sensor means, values set by the user, values calculated according to the user's settings.

According to further embodiments of the invention, the control unit is programmed to calculate either the first datum (i1) relating to the blood flow removed from the patient or the second datum (i2) relating to the flow of liquid across the tract 13; in any case, calculation of the first datum (i1) or the second datum (i2) is a function of the third datum (i3) relating to the infusion liquid flow $Q_{inf}$.

Figure 3:
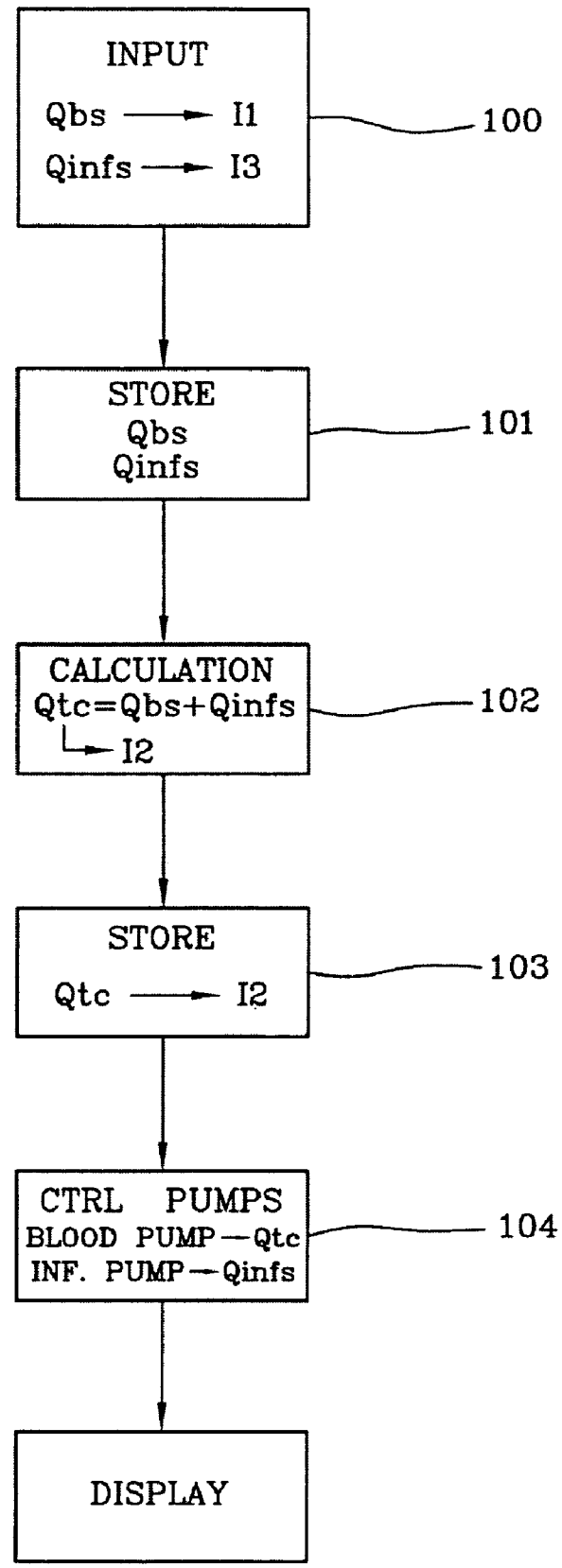
FIG. 3 is a block diagram schematically illustrating a possible operating mode of a device for calculating the blood flow rate, usable for example with the apparatus of FIGS. 1 and 2.

In the illustrated embodiment of FIG. 3, input of the first and third data are made (stage 100). For example, the user enters the desired values on an input organ for the infusion flow $Q_{infs}$ along the line 15 and for the blood flow removed from the patient $Q_{bs}$. The input stage can be done through the user interface 30 or through a card, disk or other data-support-reading system.

Alternatively, the setting values could already have been pre-stored in the computer memory 26. At this point the memory 26 has stored the first and third data (stage 101) and the control unit is able to calculate (stage 102) the second datum i2 relating to the liquid flow $Q_t$ across the tract, as a function f(i1, i3) of the third datum relating to the infusion liquid flow $Q_{inf}$ and the first datum. In the embodiment i1 corresponds to $Q_{bs}$, i3 to $Q_{infs}$ and i2, or $Q_{tc}$, is calculated as the sum of $Q_{bs}+Q_{infs}$. Subsequently (stage 103) the value calculated for $Q_{tc}$ is stored and used by the control unit 27, as will be better described herein below. If, instead (see FIG. 4), stage 100 includes input (done according to the above-described modalities) of the desired infusion flow $Q_{infs}$ values (third datum) along the line 15 and the overall flow of liquid $Q_{ts}$ (second datum) in the tract 13, then the memory stores the second and third data (stage 101), and the control unit 27 is able to calculate the first datum i1, which is a calculated value $Q_{bc}$ of the blood flow $Q_b$, as a function f(i2,i3) of the third datum (stage 102):

$$Q_{bc}=Q_{ts}-Q_{infs}$$

Returning to FIGS. 1 and 2, the device 25 comprises first sensors 28 connected to the control unit 27 and predisposed to emit a first signal 28a relating to a actual value ($Q_{tr}$) of the liquid flow crossing the tract 13. The device 25 also includes second sensors 29 connected to the control unit 27 and predisposed to provide a second signal 29a relating to a actual value $Q_{infr}$ of the liquid flow crossing the infusion line 15. The first sensors 28 can comprise (as in the embodiment illustrated in FIG. 1) a velocity sensor associated to the first pump 14 and able to send to the control unit 27 a signal expressing the velocity or angular position of the pump. The control unit 27 is thus programmed to calculate the actual value of the liquid flow $Q_{tr}$ across the tract as a function of the signal giving the angular velocity of the first pump. In an embodiment wherein the pump 14 is a peristaltic pump, the control unit 27 can be programmed to calculate the actual flow rate Qtr as a function of the signal 28a, as well as one or more of the following parameters: the geometric characteristics of the blood removal branch, possibly a time variable predisposed to take account of the time passed from the start of the extracorporeal treatment, the prevailing pressure upstream of the pump 14 (in this case a pressure sensor—not illustrated in the figures of the drawings—is included). Alternatively, as shown in FIG. 2, first sensor means comprises a liquid flow sensor associated to the blood removal branch, downstream of the connection section between the infusion line and the extracorporeal circuit. The sensor, for example mechanical or electromagnetic, emits a signal, which is directly linked to the actual liquid flow $Q_{tr}$ through branch 13.

The second sensor means comprises a weight sensor associated to the container and predisposed to send a signal to the control unit 27, instantaneously giving the weight of the container.

The control unit 27 contacts the weight sensor at certain intervals and as a result calculates the actual flow crossing the infusion line according to the actual weight values received in successive instants. The intervals can be identical, or in any case are known and calculable using a rule known to control unit 27.

In the embodiment of FIG. 3, the control unit 27 is programmed to receive the first signal 28a and to cooperate with the first movement means 14 to bring the actual liquid flow $Q_{tr}$ across the tract 13 towards the calculated value $Q_{tc}$ of the liquid flow (stage 104). Still with reference to the embodiment of FIG. 3, the control unit 27 is also programmed to cooperate with the second movement means 18 to bring the actual infusion liquid flow towards the set value $Q_{infs}$. In other words, the control unit 27 receives set values $Q_{bs}$, $Q_{infs}$ for flows $Q_b$ e $Q_{inf}$, calculates $Q_{tc}$ and regulates (control signals 28b and 29b) the actual flows across the line 15 and the tract 13 so that they respectively follow values $Q_{infs}$ and $Q_{tc}$.

Figure 4:
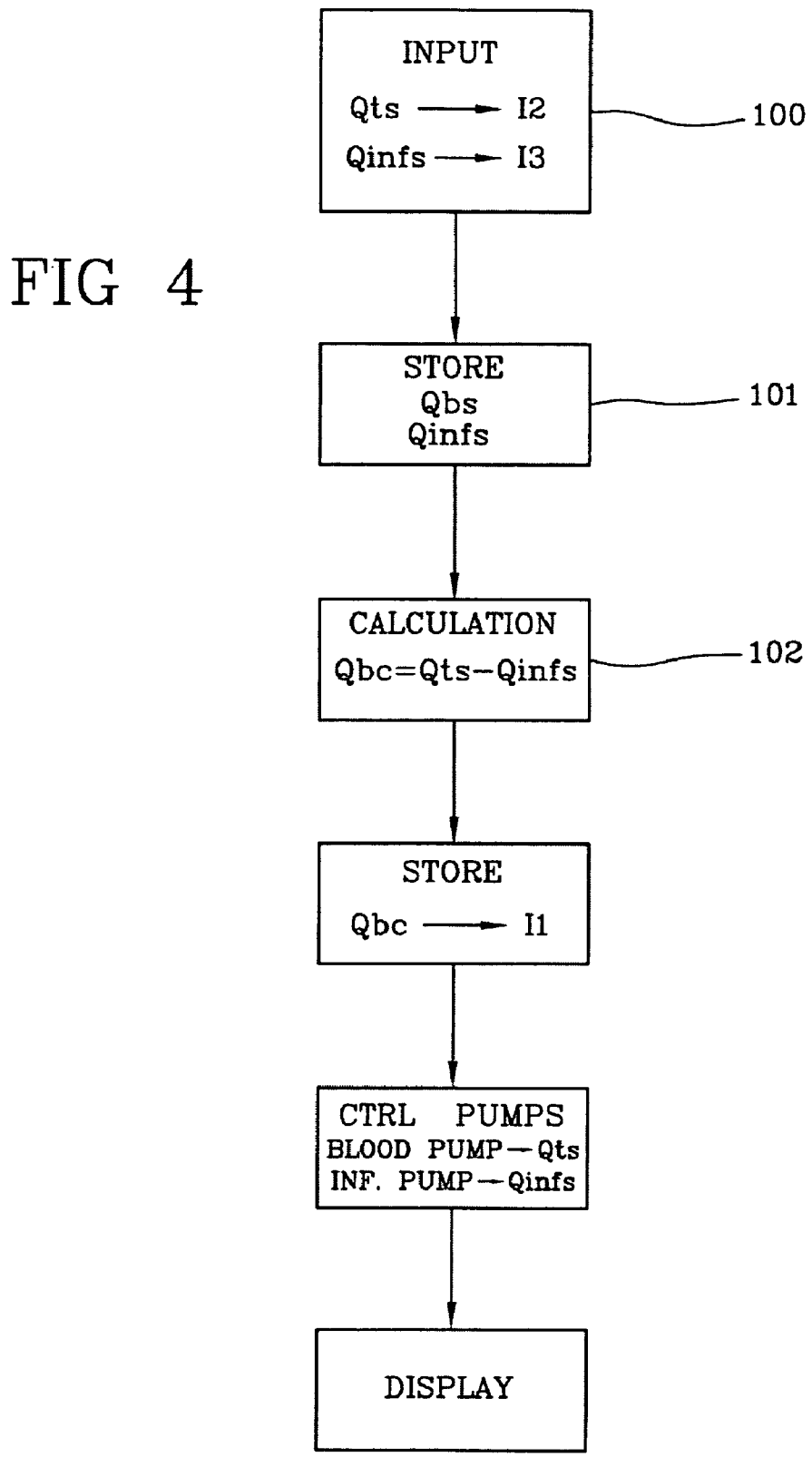
FIG. 4 is a block diagram schematically illustrating a further possible operating mode of a device for determining the blood flow rate, usable for example with the apparatus of FIGS. 1 and 2.

In the embodiment of FIG. 4, the control unit 27 is programmed to receive the first signal 28a and to cooperate with the first movement means 14 to bring the actual liquid flow $Q_{tr}$ across the tract 13 towards the set value $Q_{ts}$ of the liquid flow (stage 104). Still with reference to the embodiment of FIG. 4, the control unit 27 is also programmed to cooperate with the second movement means 18 in order to bring the actual flow of infusion liquid towards the set value $Q_{infs}$. In this second example, the actual values of the flows on the line 15 and the tract 13 are regulated (control signals 28b, 29b) on the set values Qts and Qinfs, while the value of Qb is calculated (Qbc) and is for example brought up on a display 30. For the sake of completeness, though this does not influence the present invention, note that in the embodiment of FIG. 4 there are also infusion lines 19 and 20 with respective weight sensors 50, 51 which emit corresponding signals 50a, 51a to the control unit 27, which control unit 27 also controls the pumps 23, 24 with corresponding signals 50b, 51b.

The invention is susceptible to many variants.

A further embodiment (not illustrated) is possible in which the first datum comprises a actual value of the blood flow removed from the patient, the second datum comprises a actual value of the liquid flow across the tract 13 and a third datum comprises a actual value of the infusion liquid flow. In other words, the device 25 could simply take actual flow values, read by the first sensors connected to the control unit 27 and predisposed to emit a first signal relating to a actual value (Qtr) of the liquid flow crossing the tract 13, and second sensors connected to the control unit 27 and predisposed to provide a second signal relating to a actual value (Qinfr) of the liquid flow crossing the infusion line. In this case the control unit 27 would be programmed to calculate a actual value of the blood flow removed from the patient ($Q_{br}$) using the equation $Q_{br}=Q_{tr}-Q_{infr}$ and then to send data up on the display, without any control activity taking place, but simply providing information on the status of the actual flows.

In a still further embodiment the control unit 27 could be programmed to activate only the second movement means in a case where the actual value measured for flow $Q_{tr}$ across the tract 13 differed from the set value $Q_{ts}$ (FIG. 4) or the calculated value (FIG. 3), in order to change only the infusion flow and bring the actual flow value in the tract 13 to value $Q_{ts}$ or $Q_{tc}$.

In the most typical case, however, the control unit 27 is programmed to cooperate both with the first and with the second movement means in order to bring the actual value of the flow Qtr across the tract 13 towards the set value Qts or towards the calculated value Qtc of the liquid flow across the predetermined tract 13. Apart from having specific settings both for the removed blood (or the total flow across the tract 13) and for the infusion flow, it is alternatively possible to set only the patient blood removal flow (or obviously the total flow in the tract 13) and to set a fixed ratio between the patient blood removal flow and the infusion flow. In this case, for example, the following would result: set value for blood flow Qb=$Q_{bs}$, and calculated value for infusion flow Qinf=$Q_{infc}$=K*$Q_{bs}$. The above is especially interesting when the line 15 is used for infusing anticoagulant. In this embodiment of the invention, the control unit 27 guarantees that during treatment (or during a relevant or re-set part of the treatment), the user can modify one of the set values of Qb or Qt or Qinf. In this case the control unit 27 will operate on the first and second movement means in order to reach the new setting entered by the user, while keeping the ratio K unaltered.

The ratio K can be constant (typical situation) or can take on a time-variable value according to pre-set values or a known time rule.

In a further aspect of the invention, the machine is set (or the setting is prestored in the machine memory) for a limit value of one or more of flows $Q_b$, $Q_{infs}$, $Q_t$. In each of the above-described variants the machine is predisposed to check, at intervals, that the limit thresholds are not exceeded. According to the variants, the control unit 27 can be predisposed to signal (with an alarm) that the limit has been reached (for example in a case where an infusion is activated during a treatment in which a maximum limit has been set on Qt); in the embodiment in which the control unit 27 can coordinate the first and second movement means in order to guarantee the proportionality (the above-mentioned K ratio) between the active flows, the control unit 27 can be programmed to respect the proportionality constant upon changing the setting of any one of the flows, at the same time checking that no flow exceeds its threshold limit of acceptability and positively preventing a change in any flow if that change would cause one or more of the flows to exceed a limit of acceptability.

Finally, the apparatus 1 comprises a display or user interface 30 which is connected to the control unit 27. The user interface 30 is predisposed to display at least one of the following values:
  set value (Qbs) of blood flow (Qb) removed from patient,
  set value (Qts) of liquid flow crossing the tract,
  set value (Qinfs) of infusion flow.
  calculated value (Qtc) of liquid flow crossing the tract,
  calculated value (Qbc) of blood flow (Qb) removed from the patient,
  actual value (Qbr) of blood flow (Qb) removed from the patient,
  actual value (Qtr) of liquid flow crossing the tract,
  actual value (Qinfr) of infusion flow.
  The interface is predisposed to receive in input at least one of following values, settable by a user:
    set value (Qbs) of blood flow (Qb) removed from patient,
    set value (Qts) of liquid flow crossing the tract,
    set value (Qinfs) of infusion flow.
    K constant ratio of proportionality between flow Qinf and flow Qb (or between Qinf and Qt, depending on the case).

The invention claimed is:

1. An apparatus for extracorporeal blood treatment, comprising:
  at least one blood treatment unit having a first chamber and a second chamber separated by a semi-permeable membrane;
  an extracorporeal circuit for circulation of blood, said extracorporeal circuit comprising a blood removal branch and a blood return branch, said blood removal branch having an end destined to be connected with a cardiovascular system of a patient and another end in communication with an inlet of said first chamber, said blood return branch having an end destined to be connected to a cardiovascular system of a patient and another end in communication with an outlet of said first chamber;
  first movement means operating on a post-infusion tract of said blood removal branch, said first movement means causing a flow of liquid across said extracorporeal circuit;
  an infusion line connected to said blood removal branch at a section thereof located upstream of said post-infusion tract with reference to a blood circulation direction of blood in said extracorporeal circuit;
  second movement means operating on said infusion line for causing a flow of infusion liquid across the infusion line;
  a blood flow calculation device comprising:
  a memory for receiving and storing a first datum or a second datum and for receiving and storing a third datum, said first datum relating to a flow of blood removed from the patient, said second datum being the flow of liquid across said post-infusion tract, and said third datum relating to a flow of infusion liquid flowing through said infusion line;
  first sensor means predisposed to emit a first signal relating to an actual value of the flow of liquid across said post-infusion tract;
  a user interface predisposed to receive in input said first datum, said first datum comprising a set value of the blood flow removed from the patient; and
  a control unit connected to said memory and to said user interface, said control unit being programmed to calculate said second datum as a function of said first datum and said third datum,
  said control unit being connected to said first sensor means,
  said control unit being programmed to cooperate with the first and second movement means for bringing the actual value of the flow of liquid across said post-infusion tract towards a set value of the flow of liquid across the same post infusion tract or towards said calculated second datum.

2. The apparatus of claim 1, wherein:
  said first datum comprises a set value of ($Q_{bs}$) of the blood flow removed from the patient;
  said second datum comprises a calculated value ($Q_{tc}$) of the flow liquid crossing the said post-infusion tract;
  said third datum comprises a set value ($Q_{infs}$) of the infusion flow; and
  said control unit is programmed to determine the calculated value of the liquid flow using equation $Q_{tc}=Q_{infs}+(Q_{bs})$.

3. The apparatus of claim 2, wherein said control unit is programmed to receive said first signal and to cooperate with said first movement means in order to bring the actual flow of liquid ($Q_{tr}$) across said post-infusion tract towards the calculated value ($Q_{tc}$) of the liquid flow.

4. The apparatus of claim 2, comprising second sensor means connected to said control unit and predisposed to provide a second signal relating to an actual value ($Q_{infr}$) of the flow of liquid crossing the infusion line.

5. The apparatus of claim 4, wherein the control unit is programmed to cooperate with said second movement means in order to bring the actual flow of infusion liquid towards the set value ($Q_{infs}$).

6. The apparatus of claim 2, wherein the control unit is programmed to cooperate with said second movement means in order to bring the actual flow of infusion liquid towards the set value ($Q_{infs}$).

7. The apparatus of claim 2, wherein the control unit is programmed to receive the first signal and to cooperate with the first movement means for bringing the actual liquid flow ($Q_{tr}$) across said post-infusion tract towards the set value ($Q_{ts}$) of the flow of liquid.

8. The apparatus of claim 1, wherein:
said first datum comprises a set value of ($Q_{bs}$) of the blood flow removed from the patient;
said second datum comprises a calculated value ($Q_{tc}$) of the flow liquid crossing said post-infusion tract;
said third datum comprises an actual value ($Q_{infr}$) of the infusion flow; and
said control unit is programmed to determine the calculated value of the liquid flow using equation $Q_{tc}=Q_{infr}+(Q_{bs})$.

9. The apparatus of claim 1, wherein the user interface is predisposed to display at least one value of the following values:
set value ($Q_{bs}$) of blood flow removed from patient;
set value ($Q_{ts}$) of liquid flow crossing the post-infusion tract;
set value ($Q_{infs}$) of infusion flow;
calculated value ($Q_{tc}$) of liquid flow crossing the post-infusion tract;
calculated value ($Q_{bc}$) of blood flow removed from the patient;
actual value (Qbr) of blood flow removed from the patient;
actual value ($Q_{tr}$) of liquid flow crossing the post-infusion tract;
actual value ($Q_{infr}$) of infusion flow.

10. The apparatus of claim 9, wherein the user interface is predisposed to receive in input at least one value of the following values which can be pre-set by a user:
set value ($Q_{ts}$) of liquid flow crossing the post-infusion tract;
set value ($Q_{infs}$) of infusion flow.

11. The apparatus of claim 1, wherein said control unit is programmed to receive and store in the memory at least one value from the following values:
a desired value relating to a quotient between the infusion flow ($Q_{inf}$) and the flow of blood removed from the patient, the value being fixed or obeying a pre-set time rule; or
a desired value relating to a quotient between the infusion flow ($Q_{inf}$) and the flow of liquid crossing the tract, the value being fixed or according to a pre-set time rule.

12. The apparatus of claim 11, wherein the user interface enables the user to change at least one value of the following values during the extracorporeal treatment:
set value ($Q_{bs}$) of blood flow removed from patient;
set value ($Q_{ts}$) of liquid flow crossing the post-infusion tract;
set value ($Q_{infs}$) of infusion flow;
the control unit being programmed to cooperate with at least one of the first and second movement means for maintaining the quotient between the infusion flow ($Q_{inf}$) and the blood flow removed from the patient at a level corresponding to a respective desired value.

13. The apparatus of claim 11, wherein the user interface enables the user to change at least one value of the following values during the extracorporeal treatment:
set value ($Q_{bs}$) of blood flow removed from patient;
set value ($Q_{ts}$) of liquid flow crossing said post-infusion tract;
set value ($Q_{infs}$) of infusion flow;
the control unit being programmed to cooperate with at least one of the first and second movement means for maintaining the quotient between the infusion flow ($Q_{inf}$) and the flow of liquid crossing the post-infusion tract at a level corresponding to a respective desired value.

14. The apparatus of claim 1, wherein the infusion liquid comprises anticoagulant.

15. The apparatus of claim 1, wherein the first movement means comprise a first pump operating on the blood removal branch.

16. The apparatus of claim 1, wherein the second movement means comprise a second pump operating on the infusion line.

17. The apparatus of claim 1, wherein the infusion line comprises at least one container of a liquid to be infused.

18. The apparatus of claim 1, comprising second sensor means connected to said control unit and predisposed to provide a second signal relating to an actual value ($Q_{infr}$) of the flow of liquid crossing the infusion line, said second sensor means comprising a weight sensor operatively associated to the container and predisposed to send a signal to the control unit, said signal corresponding to an updated weight of the container.

19. The apparatus of claim 1, comprising first sensor means connected to said control unit and predisposed to emit a first signal relating to an actual value ($Q_{tr}$) of the flow of liquid across said post-infusion tract, said first sensor means comprising a liquid flow sensor associated to the blood removal branch, and located downstream of a section of connection between the infusion line and the extracorporeal circuit.

20. The apparatus of claim 1, comprising first sensor means connected to said control unit and predisposed to emit a first signal relating to an actual value ($Q_{tr}$) of the flow of liquid across said post-infusion tract, said first sensor means comprising a velocity sensor associated to the first movement means and configured to send a signal to the control unit, said signal relating to an angular velocity of the first movement means.

21. The apparatus of claim 1, wherein the control unit is programmed to calculate an actual value of the flow of liquid ($Q_{tr}$) across said post-infusion tract as a function of the signal relating to an angular velocity of the first movement means, of a signal relating to an existing pressure upstream of the post-infusion tract, of geometric characteristics of the blood removal branch and of a time variable.

22. An apparatus for extracorporeal blood treatment, comprising:
at least one blood treatment unit having a first chamber and a second chamber separated by a semi-permeable membrane;
an extracorporeal circuit for circulation of blood, said extracorporeal circuit comprising a blood removal branch and a blood return branch, said blood removal branch having an end destined to be connected with a cardiovascular system of a patient and another end in communication with an inlet of said first chamber, said blood return branch having an end destined to be connected to a cardiovascular system of a patient and another end in communication with an outlet of said first chamber;

first movement means operating on a post-infusion tract of said blood removal branch, said first movement means causing a flow of liquid across said extracorporeal circuit;

an infusion line connected to said blood removal branch at a section thereof located upstream of said post-infusion tract with reference to a blood circulation direction of blood in said extracorporeal circuit;

second movement means operating on said infusion line for causing a flow of infusion liquid across the infusion line; and a blood flow calculation device comprising:

a memory for receiving and storing a first datum or a second datum and for receiving and storing a third datum, said first datum relating to a flow of blood removed from the patient, said second datum being the flow of liquid across said post-infusion tract, and said third datum relating to a flow of infusion liquid flowing through said infusion line;

first sensor means predisposed to emit a first signal relating to an actual value of the flow of liquid across said post-infusion tract;

a user interface predisposed to receive in input said first datum, said first datum comprising a set value of the blood flow removed from the patient, and said third datum comprising a set value of the flow of infusion liquid lowing through said infusion line, and said blood flow calculation device further comprising a control unit connected to said memory and to said user interface, said control unit being programmed to calculate said second datum as a function of said first datum and said third datum, said control unit being connected to said first sensor means, said control unit being programmed to cooperate with the first and second movement means for bringing the actual value of the flow of liquid across said post-infusion tract towards a set value of the flow of liquid across the same post infusion tract or towards said calculated second datum.

23. An apparatus for extracorporeal blood treatment, comprising:

at least one blood treatment unit having a first chamber and a second chamber separated by a semi-permeable membrane;

an extracorporeal circuit for circulation of blood, said extracorporeal circuit comprising a blood removal branch and a blood return branch, said blood removal branch having an end destined to be connected with a cardiovascular system of a patient and another end in communication with an inlet of said first chamber, said blood return branch having an end destined to be connected to a cardiovascular system of a patient and another end in communication with an outlet of said first chamber;

first movement means operating on a post-infusion tract of said blood removal branch, said first movement means causing a flow of liquid across said extracorporeal circuit;

an infusion line connected to said blood removal branch at a section thereof located upstream of said post-infusion tract with reference to a blood circulation direction of blood in said extracorporeal circuit;

second movement means operating on said infusion line for causing a flow of infusion liquid across the infusion line; and a blood flow calculation device comprising:

a memory for receiving and storing a first datum or a second datum and for receiving and storing a third datum, said first datum relating to a flow of blood removed from the patient, said second datum being the flow of liquid across said post-infusion tract, and said third datum relating to a flow of infusion liquid flowing through said infusion line;

first sensor means predisposed to emit a first signal relating to an actual value of the flow of liquid across said post-infusion tract; and a user interface predisposed to receive in input said first datum, said first datum comprising a set value of the blood flow removed from the patient, said user interface being also predisposed to receive in input said third datum, said third datum comprising a value of the flow of infusion liquid flowing through said infusion line, or a ratio between the blood flow removed from the patient and the value of the flow of infusion liquid flowing through said infusion line, and said blood flow calculation device further comprising a control unit connected to said memory and to said user interface, said control unit being programmed to calculate said second datum as a function of said first datum and said third datum, said control unit being connected to said first sensor means, said control unit being programmed to cooperate with the first and second movement means for bringing the actual value of the flow of liquid across said post-infusion tract towards a set value of the flow of liquid across the same post infusion tract or towards said calculated second datum.

* * * * *

UNITED STATES PATENT AND TRADEMARK OFFICE
CERTIFICATE OF CORRECTION

PATENT NO. : 7,875,168 B2  
APPLICATION NO. : 10/975082  
DATED : January 25, 2011  
INVENTOR(S) : Jean Louis Fressinet et al.

It is certified that error appears in the above-identified patent and that said Letters Patent is hereby corrected as shown below:

In Claim 22, col. 11, line 31, "lowing" should read --flowing--.

Signed and Sealed this
Twenty-sixth Day of April, 2011

David J. Kappos
*Director of the United States Patent and Trademark Office*